(12) United States Patent
Hall

(10) Patent No.: US 11,988,509 B2
(45) Date of Patent: May 21, 2024

(54) PORTABLE FIELD IMAGING OF PLANT STOMATA

(71) Applicant: Inari Agriculture Technology, Inc., Cambridge, MA (US)

(72) Inventor: Giles Hall, Medford, MA (US)

(73) Assignee: Inari Agriculture Technology, Inc., Cambridge, MA (US)

(*) Notice: Subject to any disclaimer, the term of this patent is extended or adjusted under 35 U.S.C. 154(b) by 133 days.

(21) Appl. No.: 17/774,105

(22) PCT Filed: Nov. 25, 2020

(86) PCT No.: PCT/US2020/062189
§ 371 (c)(1),
(2) Date: May 3, 2022

(87) PCT Pub. No.: WO2021/108522
PCT Pub. Date: Jun. 3, 2021

(65) Prior Publication Data
US 2022/0415066 A1 Dec. 29, 2022

Related U.S. Application Data

(60) Provisional application No. 62/940,743, filed on Nov. 26, 2019.

(51) Int. Cl.
*G06V 10/762* (2022.01)
*G01C 11/10* (2006.01)
(Continued)

(52) U.S. Cl.
CPC ......... *G01C 11/10* (2013.01); *G01N 33/0098* (2013.01); *G06V 10/44* (2022.01);
(Continued)

(58) Field of Classification Search
CPC .... G01C 11/10; G01N 33/0098; G06V 10/44; G06V 10/762; G06V 10/82;
(Continued)

(56) References Cited

U.S. PATENT DOCUMENTS

2007/0044445 A1    3/2007  Spicer et al.
2017/0359522 A1*  12/2017  Park ................... H04N 23/67
(Continued)

OTHER PUBLICATIONS

Arganda-Carreras et al., (2017). "Trainable Weka Segmentation: a machine learning tool for microscopy pixel classification," Bioinformatics, 33(15):2424-2426.
(Continued)

*Primary Examiner* — Stephen P Coleman
(74) *Attorney, Agent, or Firm* — Morrison & Foerster LLP

(57) ABSTRACT

Examples of the disclosure describe systems and methods for identifying, quantifying, and/or characterizing plant stomata. In an example method, a first set of two or more images of a plant leaf representing two or more focal distances is captured via an optical sensor. A reference focal distance is determined based on the first set of images. A second set of two or more images of the plant leaf is captured via the optical sensor, including at least one image captured at a focal distance less than the reference focal distance, and at least one image captured at a focal distance greater than the reference focal distance. A composite image is generated based on the second set of images. The composite image is
(Continued)

provided to a trainable feature detector in order to determine a number, density, and/or distribution of stomata in the composite image.

22 Claims, 7 Drawing Sheets

(51) Int. Cl.
*G01N 33/00* (2006.01)
*G06V 10/44* (2022.01)
*G06V 10/82* (2022.01)
*G06V 20/69* (2022.01)
*H04N 23/67* (2023.01)
*G06V 20/68* (2022.01)

(52) U.S. Cl.
CPC ............ *G06V 10/762* (2022.01); *G06V 10/82* (2022.01); *G06V 20/693* (2022.01); *H04N 23/67* (2023.01); *G06V 20/68* (2022.01)

(58) Field of Classification Search
CPC ...... G06V 20/693; G06V 20/68; H04N 23/67; G06F 18/24137; G06T 2207/10148; G06T 2207/20021; G06T 2207/20081; G06T 2207/20084; G06T 2207/20221; G06T 2207/30168; G06T 2207/30242; G06T 5/50; G06T 7/0008
USPC .......................................................... 382/110
See application file for complete search history.

(56) References Cited

U.S. PATENT DOCUMENTS

2018/0313760 A1   11/2018   Kramer et al.
2019/0064363 A1    2/2019   Redden et al.

OTHER PUBLICATIONS

Driscoll et al., (2005). "Specificallon of adaxial and abaxial stomata, epidermal structure and photosynthesis to $CO_2$ enrichment in maize leaves," J Exp Bot., 57(2):381-390.

Fetter et al., (2019). "StomataCounter: a neural network for automatic stomata identification and counting," New Phytologist, 223:1671-1681.

International Search Report and Written Opinion received for International Patent Application No. PCT/US2020/062189 dated Feb. 17, 2021, 13 pages.

Kremling et al., (2019). "Transcriptome-Wide Association Supplements Genome-Wide Association in *Zea mays*," G3, 9:3023-3033.

Laga et al., (2014). "Image-based Plant Stomata Phenotyping," Retrieved from the Internet <https://ieeexplore.ieee.org/stamp/stamp.jsp?tp=&amumber=7064307>, 6 pages.

Santos et al., (1997). "Evaluation of autofocus functions in molecular cytogenetic analysis," J. Microscopy, 188:264-272, 9 pages.

Scharr et al., (2015). "Leaf segmentation in plant phenotyping: a collation study," Machine Vision and Applications, 27:585-606, 22 pages.

* cited by examiner

PORTABLE FIELD IMAGING OF PLANT STOMATA

CROSS REFERENCE TO RELATED APPLICATIONS

This application is a national stage application under 35 U.S.C. § 371 of International Application No. PCT/US2020/062189, filed internationally on Nov. 25, 2020, which claims the priority benefit of U.S. Provisional Application No. 62/940,743, filed Nov. 26, 2019, each of which is hereby incorporated by reference in its entirety.

FIELD

The present disclosure relates generally to image capture and analysis, and more specifically to methods and systems of image capture and analysis for plant stomata.

BACKGROUND

Plant stomata are small (micrometer-sized) pores in plant tissue that facilitate gas/water exchange between a plant and the environment. Stomata can be found in leaves, stems, and other parts of plants, particularly on the lower epidermis of plant leaves. Gasses like carbon dioxide may diffuse through the stomata (into the plant) to facilitate photosynthesis, and the oxygen byproduct may also diffuse through the stomata (out of the plant). During the gas exchange process, water vapor may also diffuse through the stomata. Some plants may open and close their stomata according to various environmental conditions. For example, plants may open stomata in conditions with high light intensity and high humidity but may close stomata during other conditions.

Assessing stomatal dynamics (particularly in situ) can provide information important for plant photosensitivity, gas exchange, and plant hydraulics. Methods have been proposed for long-term imaging of stomatal dynamics (see, e.g., www.biorxiv.org/content/10.1101/677450v1.full), but these methods are generally time-consuming. Methods that are rapid and automated are required to phenotype stomatal characteristics in the field; however, such methods are currently lacking. In addition, phenotyping large numbers of individual plants in the field requires quick and massive phenotyping in order to assess plants at a comparable developmental stage and/or under comparable environmental conditions.

There is therefore a need to characterize and study plant stomata, e.g., for phenotype-based breeding, in a rapid, yet accurate and comprehensive manner.

BRIEF SUMMARY

To meet these and other needs, examples of the disclosure describe systems and methods for identifying, quantifying, and/or characterizing plant stomata. These methods, systems, and media provide high-throughput, low-skill ways to quickly obtain thousands of data points, e.g., to characterize large numbers of individual plants, such as in a breeding program.

In an example method, a first set of two or more images of a plant leaf representing two or more focal distances are captured via an optical sensor. A reference focal distance is determined based on the first set of images. A second set of two or more images of the plant leaf is captured via the optical sensor, wherein at least one image of the second set of images is captured at a focal distance less than the reference focal distance, and wherein at least one image of the second set of images is captured at a focal distance greater than the reference focal distance. A composite image is generated based on the second set of images. The composite image is provided to a deep convolutional neural network in order to determine a number, density, and/or distribution of stomata in the composite image.

In some embodiments, the plant is a corn plant. In some embodiments, the first set of images and the second set of images are images of an abaxial surface of the plant (e.g., corn) leaf.

In some embodiments, the methods further include capturing identification data associated with the plant leaf. In some embodiments, determining the reference focal distance includes: applying a Laplace transform to a first image of the first set of images and to a second image of the first set of images; and determining a maximum focus score from a focus score for the first image and from a focus score for the second image. In some embodiments, generating the composite image includes: determining a focus score for one or more portions of a third image from the second set of images; determining a focus score for one or more portions of a fourth image from the second set of images; and combining one or more portions of the third image with one or more portions of the fourth image based on the focus score for one or more portions of the third image and the focus score for one or more portions of the fourth image. In some embodiments, the methods further include applying a difference of Gaussians transformation to the composite image. In some embodiments, the methods further include generating a map of probabilities of stomata presence. In some embodiments, the methods further include determining clusters based on the map of probabilities. In some embodiments, the first and second sets of images are captured using polarized light. In some embodiments, the first and second sets of images are captured by illuminating the optical sensor with polarized light. In some embodiments, the first and second sets of images are captured by applying a polarizing filter onto light collected by the optical sensor. In some embodiments, resolution of the second set of images is greater than resolution of the first set of images. In some embodiments, the first and second sets of images are all captured within about 5 to about 45 seconds. In some embodiments, the methods further include applying a clamp to an area of the plant leaf, wherein the clamp is configured to position the plant leaf in a fixed position with respect to the optical sensor. In some embodiments, the clamp is further configured to prevent entry of ambient light into the optical sensor. In some embodiments, the first and second sets of images are captured via the optical sensor at a magnification between 150× and 250×. In some embodiments, the first and second sets of images are captured via the optical sensor at 200× magnification. In some embodiments, the methods further include providing, via a speaker, one or more audible outputs after capturing at least one image from the first and/or second set of images. In some embodiments, the methods further include providing, via a light source or display, one or more visible outputs after capturing at least one image from the first and/or second set of images. In some embodiments, the methods further include providing, via an actuator, one or more haptic outputs after capturing at least one image from the first and/or second set of images. In some embodiments, the methods further include decomposing the composite image into constituent regions. In some embodiments, determining a number, density, and/or distribution of stomata in the composite image includes determining a number, density, and/or distribution of stomata in the constituent regions.

In some embodiments, the methods further include associating the determined number, density, and/or distribution of stomata in the composite image with a genotype of the plant. In some embodiments, the methods further include associating the determined number, density, and/or distribution of stomata in the composite image with additional plant breeding data. In some embodiments, the additional plant breeding data include genome-wide association study (GWAS) data and/or transcriptome-wide association study (TWAS) data. In some embodiments, the methods further include selecting the plant for breeding based at least in part on the determined number, density, and/or distribution of stomata in the composite image.

Further provided herein are systems for plant leaf phenotyping. In some embodiments, the systems include an optical sensor; and one or more processors configured to execute a method including: capturing, via the optical sensor, a first set of two or more images of a plant leaf representing two or more focal distances; determining a reference focal distance based on the first set of images; capturing, via the optical sensor, a second set of two or more images of the plant leaf, wherein at least one image of the second set of images is captured at a focal distance less than the reference focal distance, and wherein at least one image of the second set of images is captured at a focal distance greater than the reference focal distance; generating a composite image based on the second set of images; and providing the composite image to a deep convolutional neural network in order to determine a number, density, and/or distribution of stomata in the composite image. In some embodiments, the one or more processors are configured to execute a method according to any one of the above embodiments. In some embodiments, the systems further include an actuator (e.g., a haptic actuator). In some embodiments, the systems further include a speaker. In some embodiments, the systems further include a light source, e.g., for providing visual feedback. In some embodiments, the systems further include a power source. In some embodiments, the systems further include one or more storage media. In some embodiments, the systems further include an identifier, e.g., a barcode scanner. In some embodiments, the systems further include a locator, e.g., a GPS sensor. In some embodiments, the systems further include a communications unit or transceiver, e.g., providing one or more wired (e.g., a USB connection) and/or wireless (e.g., Bluetooth, wi-fi, or cellular) connections. In some embodiments, the system is portable.

Further provided herein are non-transitory computer-readable media storing instructions that, when executed by one or more processors, cause the one or more processors to execute a method including: capturing, via the optical sensor, a first set of two or more images of a plant leaf representing two or more focal distances; determining a reference focal distance based on the first set of images; capturing, via the optical sensor, a second set of two or more images of the plant leaf, wherein at least one image of the second set of images is captured at a focal distance less than the reference focal distance, and wherein at least one image of the second set of images is captured at a focal distance greater than the reference focal distance; generating a composite image based on the second set of images; and providing the composite image to a deep convolutional neural network in order to determine a number, density, and/or distribution of stomata in the composite image. In some embodiments, the one or more processors are configured to execute a method according to any one of the above embodiments.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

DETAILED DESCRIPTION

Figure 1:
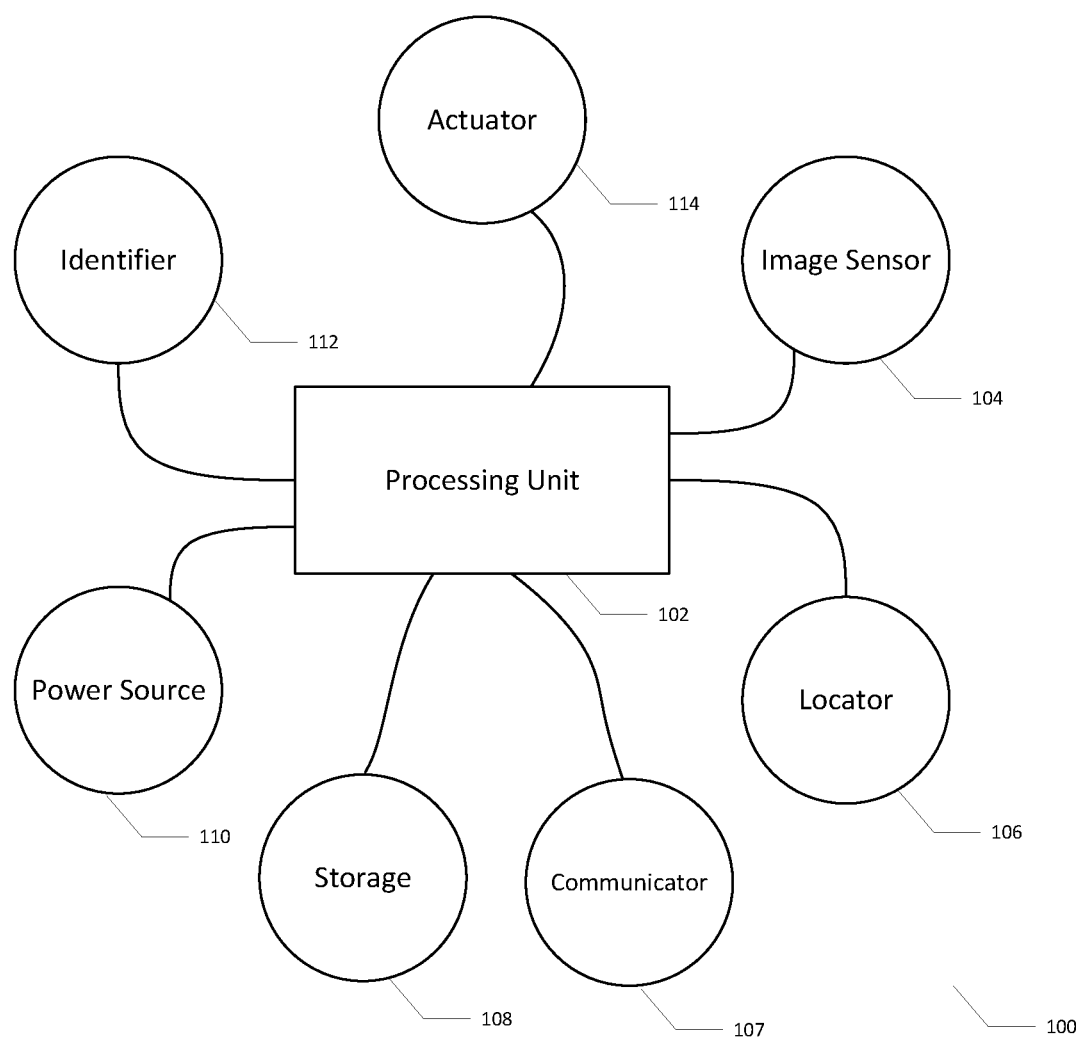
FIG. 1 illustrates an exemplary image capture system, according to some embodiments of the disclosure.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Plant stomata are pores found in various parts of a plant, including the epidermis of leaves, stems, and other plant organs. Stomata can serve important functions for plants, including being a physical interface between a plant and the environment to promote gas exchange. For example, photosynthesis is a process by which plants convert light, carbon dioxide, and water into glucose and oxygen. To facilitate photosynthesis, plants may require a mechanism to both absorb carbon dioxide and release the oxygen byproduct. A stomata can include a pore (e.g., a hole) surrounded by one or more guard cells, which may change shape to effectively open and/or close the pore, thereby permitting gas exchange (e.g., an intake of carbon dioxide and/or a release of oxygen).

However, while stomata are open, water vapor inside the plant may be lost to the environment during the gas exchange (e.g., intake of carbon dioxide). Loss of water vapor may be undesirable for plants, especially in areas where water may not be abundant. Some plants may therefore open stomata under favorable conditions and close stomata during unfavorable conditions. For example, it may be beneficial for a plant to open stomata during a period where light intensity is high and surrounding humidity is high. Because light is required to drive the photosynthesis process, it may not be advantageous for a plant to aggressively intake carbon dioxide until it has an energy source to produce glucose. High humidity may mean that the plant loses less water vapor during the gas exchange process. However, specific mechanisms used to identify and/or react to local conditions may not be comprehensively understood. It therefore can be desirable to develop systems and methods to study and characterize plant stomata to further understand mechanisms of operation.

Large scale characterization and data harvesting of stomata can be challenging for a number of reasons. Plant stomata can be small features (e.g., between 1-100 micrometers), and magnification (e.g., optical magnification) may therefore be required to study stomata. However, plants grown in fields may span large geographical areas, and outside environmental factors (e.g., inclement weather) may make it difficult to study and characterize stomata. Additionally, plant structures where stomata reside can be three-dimensional structures that may present difficulties for data collection. For example, data collection may include imaging plant organs where stomata are located (e.g., a plant leaf). The plant organ may have ridges and grooves and/or larger three-dimensional features (e.g., a general curvature of a leaf) that may present difficulties for image capture (e.g., it may be difficult to keep an entire imaged region in focus due to the three-dimensional structure of the plant organ). Furthermore, phenotyping in field conditions may be most helpful when individual plants are characterized and compared to other plants at comparable development stages. It can therefore be desirable to develop systems and methods to study and characterize plant stomata that can quickly and accurately gather data for further analysis.

FIG. 1 illustrates an example of an image capture system, according to some embodiments of the disclosure. Image capture system 100 can include a processing unit 102. Processing unit 102 can be a computing unit that may take inputs from various connected sensors and/or devices and process information received from those connected sensors and/or devices. In some embodiments, processing unit 102 can be portable, which may facilitate mobile image capture (e.g., image capture of plants in a large field). For example, processing unit 102 can be a single-board computer (e.g., a Raspberry Pi) which may be connectable to other sensors and/or devices via, for example, a USB connection and/or a wireless connection (e.g., Bluetooth). A single-board computer may include a central processing unit, memory (e.g., random access memory and/or non-volatile memory), and/or input/output connections on a single circuit board. As another example, processing unit 102 can be a mobile phone which may connect to other sensors and/or devices via wired (e.g., a USB connection) and/or wireless (e.g., Bluetooth) connections.

One or more sensors and/or devices may be connected to processing unit 102. In some embodiments, an image sensor 104 may be connected to processing unit 102. Image sensor 104 may include a camera capable of capturing images (e.g., images of plant organs). In some embodiments, image sensor 104 may include magnification components. For example, image sensor 104 may include one or more lenses that may optically magnify a view that image sensor 104 can capture, e.g., at a magnification between 100× and 300×, at a magnification between 150× and 250×, at a magnification between 175× and 225×, or at a magnification of about 200×. In some embodiments, image sensor 104 can be a microscope (e.g., an optical microscope, such as a portable optical microscope). In some embodiments, image sensor 104 can be a USB-powered microscope (e.g., a Dino-Lite digital microscope, which may operate at a magnification of approximately 200×).

In some embodiments, a locator 106 may be connected to processing unit 102. In some embodiments, a locator 106 can be used to locate image capture system 100 during operation. For example, image capture system 100 may capture images of plants in a field, and locator 106 may estimate a location for image capture system 100 during image capture. In some embodiments, the estimated location may be associated with an image captured near a time the location for image capture system 100 was estimated. Locator 106 can include a GPS unit that may estimate position based on known locations of satellites and/or base stations, a WiFi unit that may estimate position based on triangulation from known WiFi networks, and/or any other suitable hardware/software. In some embodiments, locator 106 may be used to estimate a timestamp that may be associated with a captured image.

In some embodiments, a communicator 107 may be connected to processing unit 102. In some embodiments, a communicator 107 can be used to communicate with other electronic devices (e.g., a computer, a server, and/or another image capture system). For example, communicator 107 can include a cellular modem, which may allow image capture system 100 to communicate via cellular towers. As another example, communicator 107 can include a WiFi module, which may allow image capture system 100 to access wireless networks that may be connected to the internet. Other communications means may be used as well, including wired communications (e.g., via a cable) and wireless communications (e.g., Bluetooth, ad-hoc networks, etc.). In some embodiments, communicator 107 can routinely convey acquired images to a field-located server, which may prevent loss of data in case of malfunctioning of the portable equipment.

In some embodiments, communicator 107 can convey image data to a portable image display device, such as a smartphone or tablet. Live viewing of images or seeing diagnostic codes in the filed can be beneficial for quick troubleshooting as necessary.

In some embodiments, storage 108 may be connected to processing unit 102. Storage 108 may include memory (e.g., non-volatile flash memory and/or a mechanical hard disc drive). In some embodiments, information captured by image capture system 100 may be stored in storage 108. For example, image capture system 100 may store captured images in storage 108. In some embodiments, image capture system 100 may store information associated with captured images in storage 108 (e.g., a time the image was capture, an associated location, etc.)

In some embodiments, power source 110 may be connected to processing unit 102. Power source 110 can be one or more batteries, one or more solar panels (which may be coupled to one or more controllers), and/or any other source of electricity.

In some embodiments, identifier 112 may be connected to processing unit 102. In some embodiments, identifier 112 may be used to identify an individual plant and/or plant organ. In some embodiments, identification information may be associated with a captured image. In some embodiments, identifier 112 may include a barcode scanner. Individual plants and/or plant organs may have an associated barcode that may be located on or near the plant/plant organ, and an association between the barcode and the plant/plant organ may be known. At or near a time image capture system 100 captures an image, identifier 112 may be used to identify an individual plant/plant organ and associate that information with the captured image. Identifier 112 can also include any other suitable hardware/software (e.g., a near-field communications chip). In some embodiments, identifier 112 may use a location estimate to identify and/or associate a plant with a captured image.

In some embodiments, actuator 114 may be connected to processing unit 102. In some embodiments, actuator 114 may be used to provide feedback to a user of image capture system 100. For example, actuator 114 can be a speaker, and actuator 114 may provide audio feedback (e.g., emit a noise) to indicate that an image capture cycle has begun and/or completed. In some embodiments, actuator 114 can indicate that an image is unable to be captured and/or that a captured image is low-quality. In some embodiments, actuator 114 can be a vibration motor, and actuator 114 may provide haptic feedback (e.g., a vibration pattern) to indicate information to a user of image capture system 100. In some embodiments, actuator 114 can be a light, and actuator 114 may provide visual feedback (e.g., flashing a pattern and/or changing colors) to indicate information to a user of image capture system 100. Other forms of actuators may also be used.

Figure 2:
FIG. 2 illustrates an exemplary image sensor, according to some embodiments of the disclosure.

FIG. 2 illustrates an example of an image capture system, according to some embodiments of the disclosure. In some embodiments, microscope 202 (which may correspond to image sensor 104) can be used to capture images of a plant and/or plant organs. Microscope 202 can include a light source, an image sensor, and/or one or more magnifiers (e.g., lenses). In some embodiments, a plant and/or a plant organ 204 can be fixed to microscope 202 using a clamp, e.g., using a base plate 206 (which may be attached to microscope 202) and a top plate 208 (which may be easily removable from base plate 206). Plant and/or plant organ 204 may be held in place in between base plate 206 and top plate 208, e.g., to position the plant leaf in a fixed position with respect to the optical sensor. In some embodiments, top plate 208 may connect to base plate 206 via one or more magnets 210. In some embodiments, base plate 206 can include one or more magnets 210, and top plate 206 can include one or more magnets 210 in locations that may correspond to locations of magnets in base plate 206. Magnets 210 may allow top plate 206 to be quickly removed, which may allow for quick throughput (e.g., a large number of samples may be quickly imaged). Although magnets are depicted, it is also contemplated that other methods of attaching top plate 208 to base plate 206 may be used (e.g., a hinge, springs, etc.). In some embodiments, top plate 208 can be optically opaque (or substantially optically opaque) such that little to no light is transmitted through top plate 208. It can be advantageous to use an optically opaque top plate so that external environmental light may be occluded from the plant and/or plant organ 204 being imaged by microscope 202.

In some embodiments, one or more images of the present disclosure are captured using polarized light. For example, an imaging sensor (e.g., image sensor 104, or part of microscope 202) can be illuminated with polarized light, or a polarizing filter may be applied to lens-collected light. Polarized light may be especially useful in preventing interference from other leaf features like trichomes and obtaining stomatal images of sufficient quality to be processable by downstream algorithms.

Figure 3A:
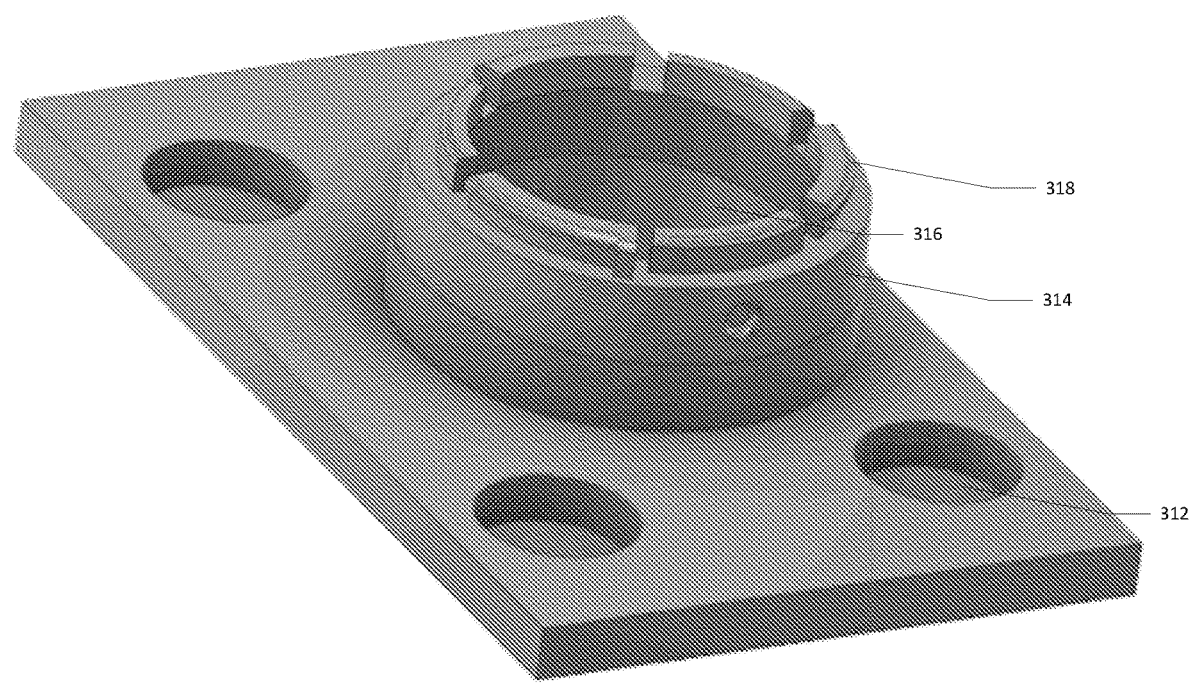
FIG. 3A illustrates a perspective view of an exemplary base plate, according to some embodiments of the disclosure.

FIG. 3A illustrates a perspective view of an exemplary base plate, according to some embodiments of the disclosure. Base plate 306 (which can correspond to base plate 206) can include one or more recesses 312. In some embodiments, base plate 306 can include four recesses 312, which may each be located near a different corner of base plate 306. In some embodiments, one or more magnets may be set in recess 312 (e.g., using adhesives). In some embodiments, base plate 306 can include a collar 314 which may define a hole 316. Hole 316 may extend through base plate 306. In some embodiments, an image sensor (e.g., microscope 202) may view a sample (e.g., plant and/or plant organ 204) through hole 316. In some embodiments, collar 314 may include a fastening region 318. In some embodiments, fastening region 318 may be used to connect base plate 306 to an image sensor (e.g., microscope 202). In some embodiments, fastening region 318 can include threads which may mate with corresponding threads on an image sensor, and base plate 306 may be screwed onto the image sensor. However, other fastening methods may also be used (e.g., magnets or adhesives).

Figure 3B:
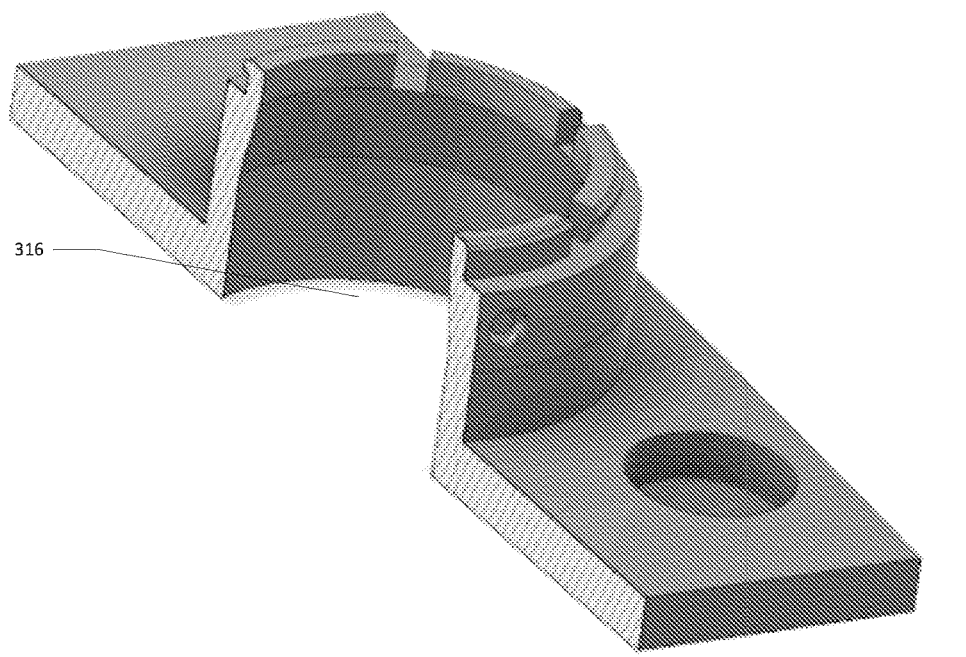
FIG. 3B illustrates a cross-sectional view of an exemplary base plate, according to some embodiments of the disclosure.

FIG. 3B illustrates a cross sectional view of an exemplary base plate, according to some embodiments of the disclosure. In some embodiments, base plate 306 can be printed from a 3D printer. In some embodiments, base plate 306 can be formed from injection molding Other suitable manufacturing techniques may be used as well.

In some embodiments base plate 306 can include scale markings, such as a grid. Scale markings can be useful for calibrating images taken with different sensors, so that manufacturing imperfections of base plates may not result in systematic differences between images acquired with different sensors.

Figure 4:
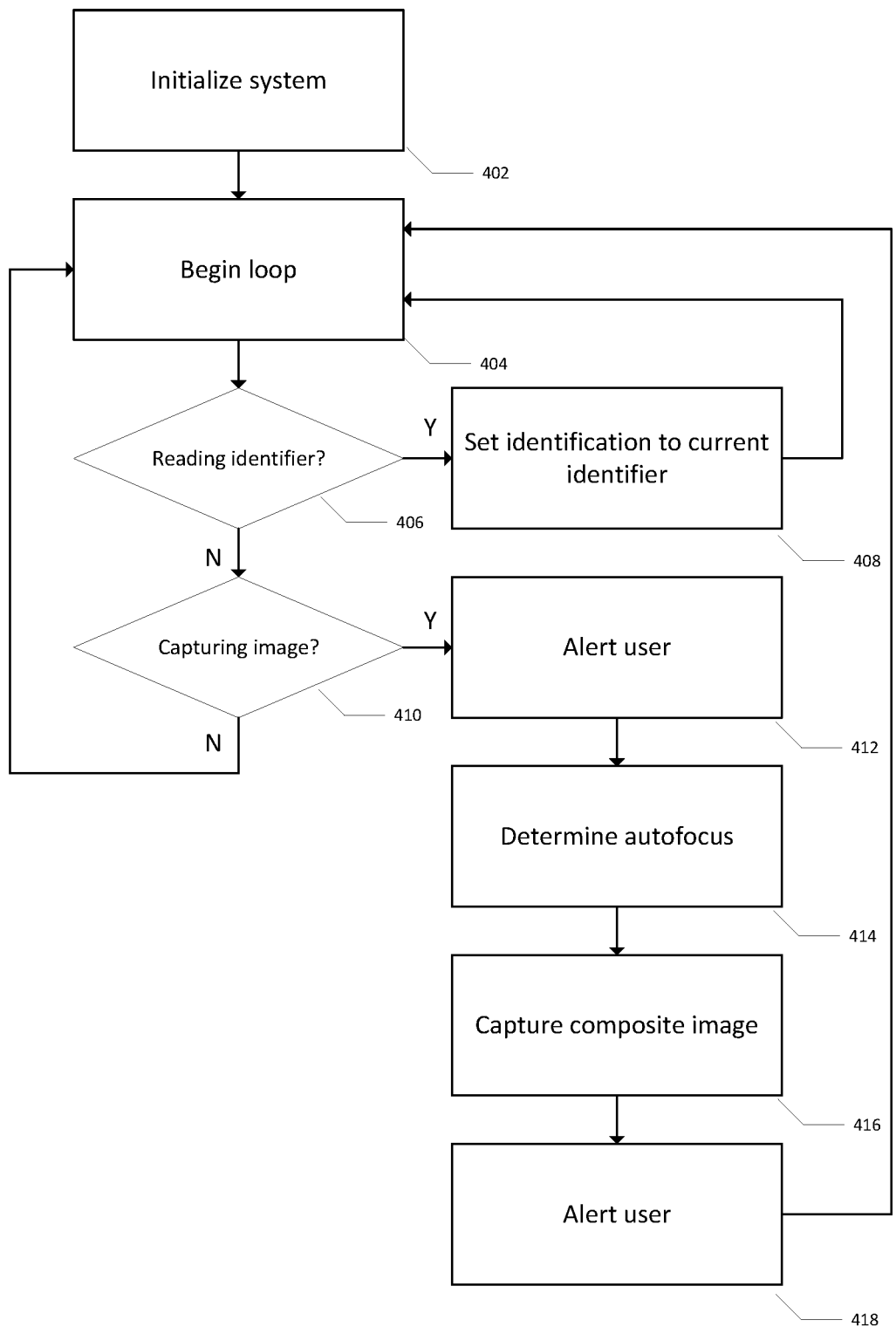
FIG. 4 illustrates an exemplary method of operation for an image capture system, according to some embodiments of the disclosure.

FIG. 4 illustrates an exemplary method for using an image capture system, according to some embodiments of the disclosure. At step 402, image capture system can be initialized. Initialization can include booting up an operating system and/or loading an application. At step 404, a software loop may begin. At step 406, it can be determined if an identifier should be read. The determination can be made through any suitable means, including prompting a user through a user interface. For example, the user may be presented with an option to read an identifier. If the user selects that option, the method may proceed to step 408. At step 408, an identifier may be read using, for example, identifier 112 (e.g., a barcode may be read using a barcode scanner). In some embodiments, the read identifier can be stored in a memory, and a captured image may be associated with the identifier. In some embodiments, if it is determined that an identifier should not be read (e.g., a user selected a user interface option corresponding with a different function), the method may proceed to step 410. At step 410, it can be determined whether an image should be captured. For example, image capture system may present a user interface option associated with image capture. If a user selects that option, the method may proceed to step 412. At step 412, an alert may be issued to a user. In some embodiments, the alert (e.g., an audible alert) may indicate that an image capture is about to take place. At step 414, an autofocus focal distance may be determined. The focal distance can be determined by any known algorithm (see, e.g. Santos et al, J. Microscopy 188:264-272, 1997). At step 416, a composite image may be captured (e.g., of a plant and/or plant organ). At step 418, an alert may be issued to a user. In some embodiments, the alert (e.g., an audible alert) may indicate that in image has been recently captured. The determinations at steps 406 and 410 can be made through any suitable means. For example, the determinations at steps 406 and/or 410 can be automated (e.g., image capture system can automatically determine whether a barcode is readable by a barcode scanner and automatically proceed to step 408).

In some embodiments, a quality control ("QC") step can follow step 410. Accordingly, an image, which may be a composite image produced at step 416 or an earlier lower resolution focusing image, can be subjected to a QC algorithm to ensure that quality data is being collected. For example, images that are deemed too out of focus, that do not capture sufficient area of a sample, and/or images that are overexposed/underexposed may be deemed insufficient quality. In case a malfunction is detected, the QC step can alert the user, which may prevent collection of faulty data. The QC algorithm can be built by training based on image feature recognition, for example building on features such as direction of stomatal rows for collecting images with optimum data for their aspect ratio. A QC algorithm may also be trained to identify proper focus or overexposed/underexposed images that may be caused by equipment and/or user error.

Figure 5:
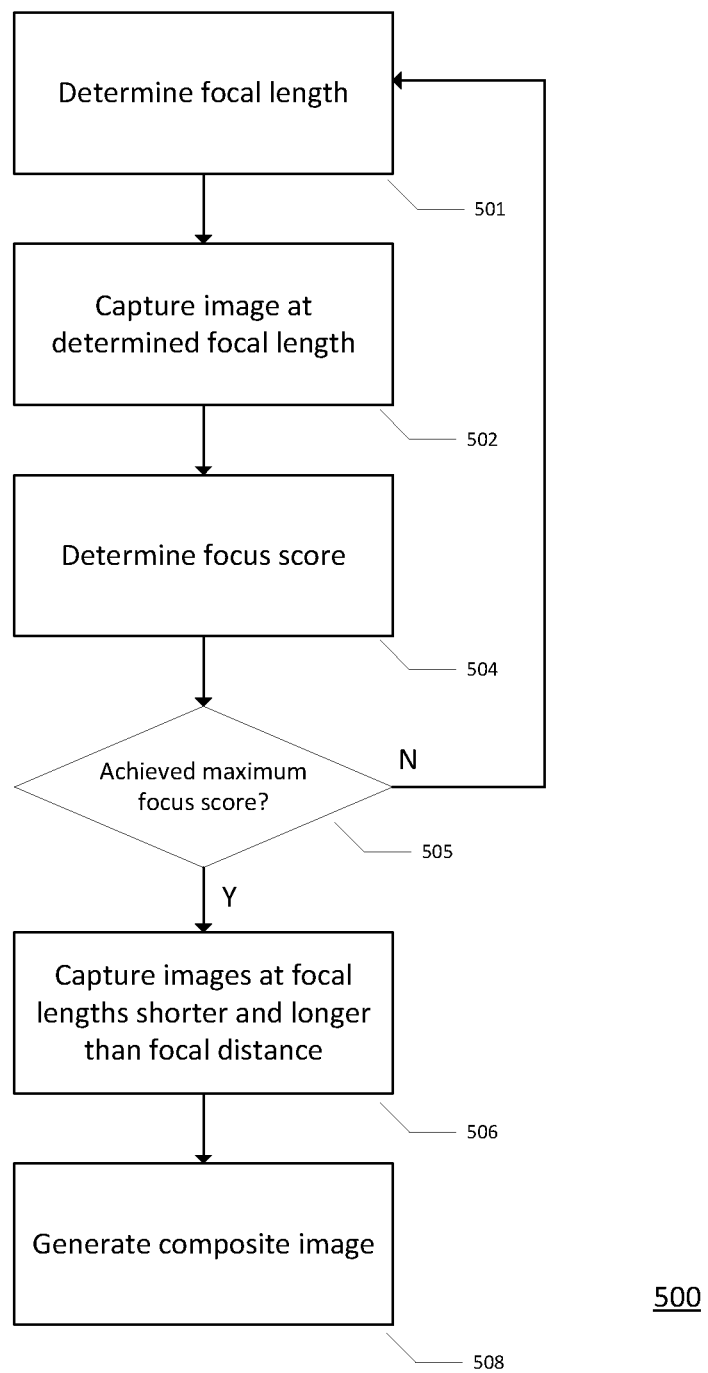
FIG. 5 illustrates an exemplary method for generating a composite image, according to some embodiments of the disclosure.

FIG. 5 illustrates an exemplary method for capturing an image, according to some embodiments of the disclosure. In some embodiments, method 500 may correspond to steps 414 and 416. At step 501, a focal length may be determined. For example, an optical microscope may include a camera with one or more movable lens elements. The lens elements may move further away and/or closer to an image sensor of the camera, which may adjust a focal length of the camera. In some embodiments, a first determined focal length can be a maximum or minimum focal length for a camera. At step 502, an image may be captured at a determined focal length (e.g., a maximum or minimum focal length for a camera).

At step 504, a focus score may be determined for a captured image. In some embodiments, a focus score may be determined by applying a Laplace transform to the captured image. For example, a Laplacian transform may be applied to the pixels of a captured image, and a convolution kernel may also be used. In some embodiments, the following convolution kernel may be used (although other kernels may be used as well):

$$\begin{matrix} 0 & 1 & 0 \\ 1 & -4 & 1 \\ 0 & 1 & 0 \end{matrix}$$

In some embodiments, a focus score may be based on the highest magnitude of the sum of absolute Laplacian transform values. In some embodiments, a focus score may be based on a variance of the Laplacian transform function. In some embodiments, a focus score may be determined directly from a captured image. In some embodiments, a captured image may be processed prior to determining a focus score. For example, an image may be captured as a three-channel RGB image, but it may be converted down to an 8-bit grayscale image. It may be advantageous to process (e.g., reduce a complexity of) a captured image to simplify subsequent calculations (e.g., it may be simpler to compute a Laplace transform of a grayscale image than an RGB image).

At step 505, it can be determined if a maximum focus score has been achieved. In some embodiments, a maximum focus score may only be determined once at least two images have been captured at different focal lengths. For example, after a first image is captured at a first focal length (e.g., at a maximum focal length) and a corresponding focus score has been determined, a new focal length may be determined at step 501 (e.g., a minimum focal length). A second image may be captured at the minimum focal length, and a focus score may be determined for the second image. In some embodiments, a bisection algorithm may be used to determine an optimal focal length. For example, a focus score may be determined for an image captured at a maximum and at a minimum focal length. A focus score may then be determined for an image captured at a focal length equidistant from the maximum and minimum focal length. A focus score may be continually determined for focal lengths between two previously used focal lengths as an ideal focal length is approached. This process may be repeated until a limit is reached for how small a camera may increment its focal length, at which point an ideal focal length may be determined (e.g., based on the maximum focus score).

Once a maximum focus score has been achieved, additional images may be captured at step 506. In some embodiments, four additional images may be captured at focal lengths other than the ideal focal length. For example, two images may be captured at focal lengths longer than the ideal focal length (e.g., at a focal length one step above the ideal focal length and at a focal length two steps above the ideal focal length). In some embodiments, two images may be captured at focal lengths shorter than the ideal focal length (e.g., at a focal length one step below the ideal focal length and at a focal length two steps below the ideal focal length). It may be advantageous to capture additional images at other focal lengths in addition to the ideal focal length because a sample (e.g., a plant and/or a plant organ) may not be completely flat. Where a sample may have varying heights, it may not be feasible to capture a single image where the entire sample is in maximum focus. Advantageously, determining a reference focal distance before capturing the images used to generate a composite image (e.g., the images used for stomatal phenotyping) increases through-put by first providing a rough focal distance useful for imaging stomata, then taking images around that reference distance, thereby decreasing the amount of focusing needed per image that will be used for processing.

Although an additional four images is described above, it is also contemplated that any number of additional images may be captured, and it is also contemplated that no additional images may be captured. In some embodiments, additional images need not be centered around an ideal focal length (e.g., three images may be captured above the ideal focal length and one image may be captured below the ideal focal length). In some embodiments, additional images need not be incremented by the smallest focal length increments (e.g., one image may be captured five steps above the ideal focal length and another image may be captured ten steps above the ideal focal length). A number of additional images and how they may be distributed across focal lengths may be based on a determination of a depth variance of a sample. For example, a sample with a wide variance in three-dimensional depth may benefit from capturing a larger number of additional images and/or capturing additional images at larger focal length intervals. In some embodiments, a larger number of additional images may yield more accurate feature detection (e.g., stomata count), but may be more computationally expensive to process. In some embodiments, a set of images used to generate a composite image may have greater resolution than a set of images used to determine a reference focal distance.

In some embodiments, one or more images (e.g., the images of a first and second set of images of the present disclosure) may be captured within a specified period of time, e.g., in less than 5 minutes, less than 3 minutes, less than 1 minute, within about 5 seconds to about 60 seconds, or within about 5 seconds to about 45 seconds. In some embodiments, all images (e.g., the images of a first and second set of images of the present disclosure) may be captured within a specified period of time, e.g., in less than 5 minutes, less than 3 minutes, less than 1 minute, within about 5 seconds to about 60 seconds, or within about 5 seconds to about 45 seconds.

At step 508, a composite image may be generated from an image captured at an ideal focal length and/or images captured at other focal lengths. For example, a focus score may be determined for portions of each captured image (instead of determining a focus score for a captured image in its entirety). In some embodiments, a region size (e.g., a block of 256×256 pixels) may be used to determine focus scores of a captured image in increments of the region size. A maximum focus score may be determined for each corresponding region across all captured images. A composite image may include stitching together portions of individual captured images based on a maximum focus score for each region. In some embodiments, a composite image may include more regions in optimal focus than a single captured image.

Figure 6:
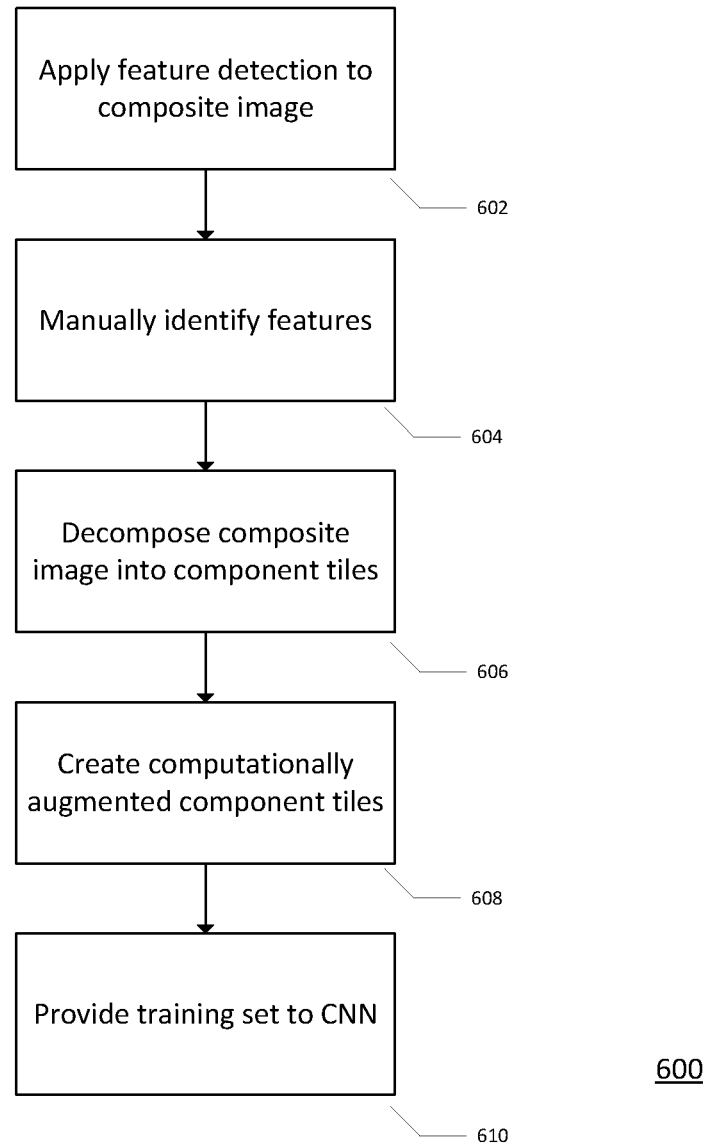
FIG. 6 illustrates an exemplary method for training a convolutional neural network, according to some embodiments of the disclosure.

FIG. 6 illustrates an exemplary method for preparing training data for machine learning algorithms, according to some embodiments of the disclosure. In some embodiments, it may be beneficial to utilize machine learning algorithms to automatically and accurately process images (e.g., to characterize and/or count stomata). Manually characterizing stomata features may be a time-consuming task, particularly if a large number of samples from a large number of plants can be analyzed. In some embodiments, it may be unfeasibly expensive and/or time-consuming to characterize a large number of samples (e.g., for phenotyping).

Machine learning algorithms can be advantageous for a number of reasons. For example, machine learning algorithms may automatically and quickly produced desired results like identifying, quantifying, and/or characterizing stomata. In some embodiments, machine learning algorithms may be robust than conventional algorithms. For example, a conventional algorithm may only be capable of identifying, quantifying, and/or characterizing stomata in ways that a programmer has specifically accounted for. A machine learning algorithm may be able to process data with unanticipated characteristics (e.g., the stomata are differently shaped or sized) based on training data provided to the machine learning algorithm. In some embodiments, machine learning algorithms may be more accurate than conventional algorithms. For example, a machine learning algorithm may improve over time with reinforcement mechanisms (e.g., if a human operator periodically performs manual checks on machine learning outputs). In some embodiments, conventional algorithms may have to be re-written and/or modified to improve the algorithm's accuracy. Many general image segmentation techniques have been developed. See, for example, Arganda-Carreras et al, Bioinformatics 2017, 33(15):2424-2426.

In some embodiments, a convolutional neural network may be particularly suited for image analysis (e.g., identification, quantification, and/or characterization of images of stomata) as a trainable feature detector. In some embodiments, a convolutional neural network may be more accurate than a generic feed-forward neural network because a convolutional neural network may be able to better identify and group complex features in a captured image. In some embodiments, a convolutional neural network may include two modules: a feature detection module and a classification module.

In some embodiments, a feature detection module may include receiving as an input a digital image including pixels. The image may be convolved using a convolution kernel of a particular size and composition (e.g., a square matrix of integers). Applying a convolution kernel may reduce an image's complexity for computational efficiency while retaining important and/or high-level feature characteristics for feature detection. In some embodiments, an image fed into a convolutional neural network may include one or more channels (e.g., an RGB image may include three channels). In some embodiments, each channel may be individually convoluted using a convolutional kernel. In some embodiments, a convolved image may optionally be pooled to further reduce an image complexity and/or reduce noise in an image. Pooling can be max pooling (e.g., a largest value in a sliding window is extracted) or average pooling (e.g., an average value within the sliding window is extracted). Other pooling methods may be used as well, or no pooling methods may be used.

In some embodiments, a classification module can include a feed-forward neural network. In some embodiments, a pooled image may be flattened (e.g., into a column vector) and fed as an input into a feed-forward neural network. In some embodiments, a feed-forward neural network may include one or more layers, wherein each layer may include one or more nodes. In some embodiments, a node may represent a function that can output a binary output (e.g., a 1 or a 0). A node may take as inputs other nodes from a prior layer, which may be accorded different weights. In some embodiments, a final layer may include one or more nodes that may output a probability that a corresponding pixel (or set of pixels) represents a stomata. In some embodiments, an actual output may be compared to a desired output and/or ground truth (e.g., a data training set) to evaluate the accuracy of the convolutional neural network. In some embodiments, corrections may be back-propagated through the convolutional neural network.

It can be beneficial to curate and/or pre-process a set of training data. In some embodiments, processed training data may yield a more accurate and/or more robust convolutional neural network and may increase a speed at which a neural network increases its accuracy. Referring still to FIG. 6, a method 600 can be used to process training data to build a more accurate and/or more robust convolutional neural network for identifying, quantifying, and/or characterizing plant stomata. At step 602, a feature detection algorithm may be applied to a composite image (which may correspond to an output from step 508). In some embodiments, a feature detection algorithm can include applying a Difference of Gaussians ("DoG") algorithm to the composite image. A DoG algorithm may convolve an image (which may be grayscale) with a first Gaussian kernel including a first standard deviation. A DoG algorithm may also convolve the same image with a second Gaussian kernel including a second standard deviation and subtract the resulting images from each other. The result may be an image with suppressed noise while retaining features (e.g., edges, lines, and/or boundaries). In some embodiments, an automated determination of stomata may be made based on the DoG-transformed composite image (e.g., using computer-vision algorithms). Alternative edge detectors may include Laplacian and Sobel filters, Hessian matrix eigenvalues, and/or Gabor filters.

At step 604, features may be manually identified. In some embodiments, automatically identified features may be corrected and/or supplemented through manual review (e.g., a human operator may manually define boundaries of stomata on a composite image). In some embodiments, all features may be manually identified (e.g., if no automated feature detection was applied).

At step 606, a composite image may be decomposed into component tiles. In some embodiments, a component image may be decomposed into component tiles of 256×256 pixels (although other tile sizes may be used as well). A composite image can be an RGB composite image, a grayscale composite image, a DoG-transformed composite image, and/or another composite image. It can be beneficial to decompose a composite image into component tiles because it may be more computationally efficient to process smaller images and/or it may result in more accurate feature detection in a convolutional neural network.

At step 608, computationally augmented component tiles may optionally be added. In some embodiments, computationally augmented component tiles can include linear transforms of original component tiles (e.g., an original component tile may be inverted, rotated, sheared, and/or modified in other ways). Computationally augmented component tiles may increase an efficacy of a training set.

At step 610, a training set may be provided to a computational neural network. In some embodiments, the training set may include original component tiles and/or computationally augmented component tiles. In some embodiments, the training set may yield a trained convolutional neural network capable of identifying, quantifying, and/or characterizing plant stomata.

Figure 7:
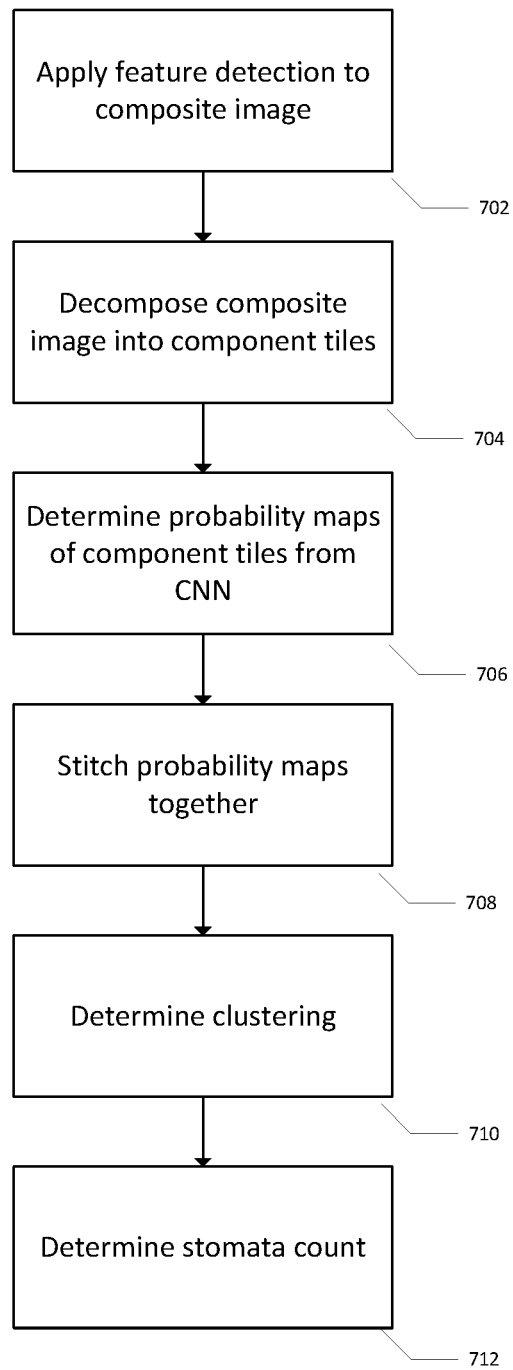
FIG. 7 illustrates an exemplary method for using a convolutional neural network to determine plant stomata characteristics, according to some embodiments of the disclosure.

FIG. 7 illustrates an exemplary method for identifying, quantifying, and/or characterizing plant stomata using a convolutional neural network, according to some embodiments of the disclosure. At step 702, a feature detection algorithm (e.g., a DoG transformation) may be applied to a composite image (which may correspond to an output from step 508).

At step 704, a composite image (which can be an RGB composite image, a grayscale composite image, a DoG-transformed composite image, and/or another composite image) can be decomposed into component tiles (e.g., of the same size component tiles as the training set).

At step 706, a probability map may be determined for a corresponding component tile. In some embodiments, a probability map can include a one-to-one, pixel-level probability that a given pixel represents a stomata and/or part of a stomata. In some embodiments, an output of a convolutional neural network (e.g., a convolutional neural network trained by method 600) may include a probability map.

At step 708, probability maps corresponding to component tiles of a composite image may be stitched together to generate a probability map corresponding to the entire composite image.

At step 710, clustering may be determined. It can be beneficial to applying clustering to a probability map corresponding to an entire composite image to classify nearby pixels as a single instance of a stomata. In some embodiments, a k-means clustering algorithm can be used. In some embodiments, a k-means clustering algorithm may identify and/or place centroids throughout a probability map (e.g., a probability map corresponding to an entire composite image). In some embodiments, a k-means clustering algorithm can minimize an average distance between points within a cluster to a cluster center. In some embodiments, a k-means clustering algorithm can maximize an average distance between cluster centers.

At step 712, a count of stomata may be determined from a clustered probability map. In some embodiments, the count may be based on the number of identified clusters. In some embodiments, other characteristics of plant stomata may be observed. For example, a size of stomata may be determined from a size of one or more clusters. In another example, a distribution of stomata may be determined from a distribution of clusters. In another example, a density of stomata may be determined from a density of clusters.

The methods, systems, and devices described herein may be applied to a variety of different plant/plant leaf types. In some embodiments, the plant has substantially flat leaves. In some embodiments, the plant is a corn plant. In some embodiments, the abaxial surface of the plant leaf is imaged.

The methods, systems, and devices described herein may find use in a variety of applications, e.g., involving rapid stomatal phenotyping of multiple plants (e.g., plants of the same species). In some embodiments, the methods, systems, and devices are used to phenotype individual plants, e.g., in the field. In some embodiments, the methods, systems, and devices are used to phenotype a plurality of individual plants, e.g., in the field.

Once data regarding one or more stomatal characteristics of a plant (e.g., number, density, and/or distribution of stomata) are obtained, these data can be associated with other data for a variety of applications. For example, data regarding one or more stomatal characteristics of a plant (e.g., number, density, and/or distribution of stomata) can be associated with a plant identifier (e.g., a barcode of the plant, as described supra).

In some embodiments, data regarding one or more stomatal characteristics of a plant (e.g., number, density, and/or distribution of stomata) may be associated with a genotype of the plant. In some embodiments, data regarding one or more stomatal characteristics of a plant (e.g., number, density, and/or distribution of stomata) may be associated with additional plant breeding data, including but not limited to genome-wide association study (GWAS) data and/or transcriptome-wide association study (TWAS) data. As is known in the art, plant breeding data such as that from GWAS or TWAS may be used to associate heritable genetic variants with one or more phenotypes of interest. Methods for obtaining and processing GWAS and TWAS data are known in the art. See, e.g., Kremling, K A G et al. (2019) *G3 (Bethesda)* 9:3023-3033.

As such, information regarding stomatal characteristics (e.g., number, density, size, area, length, width, ellipticity, distance from nearest neighbors, patterning consistency, rogue stomata, open or closed status, and/or distribution of stomata) may be used as a factor in plant breeding schemes, e.g., to select for one or more stomatal characteristics of interest, in addition to any number of additional phenotypic or genotypic features. In some embodiments, a plant may be selected for breeding based at least in part on one or more stomatal characteristics (e.g., number, density, and/or distribution of stomata) as determined herein. In some embodiments, a plant may be selected for breeding based at least in part on a genotype, genotypic feature, or genetic variant associated with one or more stomatal characteristics (e.g., number, density, and/or distribution of stomata) as determined herein.

Although the disclosed examples have been fully described with reference to the accompanying drawings, it is to be noted that various changes and modifications will become apparent to those skilled in the art. For example, elements of one or more implementations may be combined, deleted, modified, or supplemented to form further implementations. Such changes and modifications are to be understood as being included within the scope of the disclosed examples as defined by the appended claims.

What is claimed is:

1. A method for plant leaf phenotyping, comprising:
   capturing, via an optical sensor, a first set of two or more images of a plant leaf representing two or more focal distances;
   determining a reference focal distance based on the first set of images;
   capturing, via the optical sensor, a second set of two or more images of the plant leaf, wherein at least one image of the second set of images is captured at a focal distance less than the reference focal distance, and wherein at least one image of the second set of images is captured at a focal distance greater than the reference focal distance;
   generating a composite image based on the second set of images; and
   providing the composite image to a trainable feature detector in order to determine a number, density, and/or distribution of stomata in the composite image.

2. The method of claim 1, wherein the plant is a corn plant.

3. The method of claim 1, wherein the first set of images and the second set of images are images of an abaxial surface of the plant leaf.

4. The method of claim 1, further comprising capturing identification data associated with the plant leaf.

5. The method of claim 1, wherein determining the reference focal distance comprises:
   applying a Laplace transform to a first image of the first set of images and to a second image of the first set of images, wherein applying the Laplace transform comprises calculating a variance; and
   determining a maximum focus score from a focus score for the first image and from a focus score for the second image.

6. The method of claim 1, wherein generating the composite image comprises:
   determining a focus score for one or more portions of a third image from the second set of images;
   determining a focus score for one or more portions of a fourth image from the second set of images; and
   combining one or more portions of the third image with one or more portions of the fourth image based on the focus score for one or more portions of the third image and the focus score for one or more portions of the fourth image.

7. The method of claim 1, further comprising applying a difference of Gaussians transformation to the composite image.

8. The method of claim 1, further comprising generating a map of probabilities of stomata presence.

9. The method of claim 8, further comprising determining clusters based on the map of probabilities.

10. The method of claim 9, further comprising determining at least one of a size, a shape, or an opened or closed status of a stomata.

11. The method of claim 1, wherein the first and second sets of images are captured using polarized light.

12. The method of claim 1, wherein a resolution of the second set of images is greater than a resolution of the first set of images.

13. The method of claim 1, further comprising applying a clamp to an area of the plant leaf, wherein the clamp is configured to position the plant leaf in a fixed position with respect to the optical sensor.

14. The method of claim 1, wherein the first and second sets of images are captured via the optical sensor at a magnification between 150× and 250×.

15. The method of claim 1, further comprising providing, via a speaker or light source or display, one or more audible or visible outputs after capturing at least one image from the first and/or second set of images.

16. The method of claim 1, further comprising decomposing the composite image into constituent regions.

17. The method of claim 1, further comprising associating the determined number, density, and/or distribution of stomata in the composite image with a genotype of the plant and/or additional plant breeding data.

18. The method of claim 17, wherein the additional plant breeding data comprise genome-wide association study (GWAS) data and/or transcriptome-wide association study (TWAS) data.

19. The method of claim 1, further comprising selecting the plant for breeding based at least in part on the determined number, density, and/or distribution of stomata in the composite image.

20. The method of claim 1, wherein the trainable feature detector is based on a deep convolutional neural network or a random forest.

21. A system for plant leaf phenotyping, comprising:
   an optical sensor;
   one or more processors configured to execute a method comprising:
      capturing, via the optical sensor, a first set of two or more images of a plant leaf representing two or more focal distances;
      determining a reference focal distance based on the first set of images;
      capturing, via the optical sensor, a second set of two or more images of the plant leaf, wherein at least one image of the second set of images is captured at a focal distance less than the reference focal distance, and wherein at least one image of the second set of images is captured at a focal distance greater than the reference focal distance;
      generating a composite image based on the second set of images; and
      providing the composite image to a trainable feature detector in order to determine a number, density, and/or distribution of stomata in the composite image.

22. A non-transitory computer-readable medium storing instructions that, when executed by one or more processors, cause the one or more processors to execute a method comprising:
   capturing, via an optical sensor, a first set of two or more images of a plant leaf representing two or more focal distances;
   determining a reference focal distance based on the first set of images;
   capturing, via the optical sensor, a second set of two or more images of the plant leaf, wherein at least one image of the second set of images is captured at a focal distance less than the reference focal distance, and wherein at least one image of the second set of images is captured at a focal distance greater than the reference focal distance;
generating a composite image based on the second set of images; and
providing the composite image to a trainable feature detector in order to determine a number, density, and/or distribution of stomata in the composite image.

* * * * *